(12) United States Patent
Pepper et al.

(10) Patent No.: US 7,709,199 B2
(45) Date of Patent: May 4, 2010

(54) CHRONIC LYMPHOCYTIC LEUKAEMIA

(75) Inventors: Chris Pepper, Vale of Glamorgan (GB); Paul Brennan, Cardiff (GB); Naomi Price-Lloyd, Chiswick (GB); Janet E. Williams, Bridgend (GB); Jeff D. Griffiths, Mid-Glamorgan (GB); Chris Fegan, Vale of Glamorgan (GB)

(73) Assignee: University College Cardiff Consultants Limited, Cardiff (GB)

( * ) Notice: Subject to any disclaimer, the term of this patent is extended or adjusted under 35 U.S.C. 154(b) by 630 days.

(21) Appl. No.: 11/525,517

(22) Filed: Sep. 22, 2006

(65) Prior Publication Data

US 2008/0026383 A1 Jan. 31, 2008

(30) Foreign Application Priority Data

Jun. 14, 2006 (CA) .................................. 2547901

(51) Int. Cl.
*C12Q 1/68* (2006.01)
*G01N 33/53* (2006.01)
(52) U.S. Cl. ........................................... 435/6; 435/7.1
(58) Field of Classification Search .................. 435/6, 435/7.1
See application file for complete search history.

(56) References Cited

OTHER PUBLICATIONS

Shanafelt et al (Blood, Feb. 15, 2004, 103(4): 1202-1210.*
Shanafelt et al (Blood, Feb. 2004, 103(4): 1202-1210).*
Brennan et al., Inhibition of nuclear factor kappaB by direct modification in whole cells—mechanism of action of nordihydroguaiaritic acid, curcumin and thiol modifiers, *Biochem. Pharmacol.*, 55:965-73 (1998).
Chen et al., ZAP-70 directly enhances IgM signaling in chronic lymphocytic leukemia, *Blood*, 105:2036-41 (2005).
Cruse et al., ZAP-70 and CD38 as predictors of IgVH mutation in CLL, *Exp. Mol. Pathol.*, 83(3):459-61 (2007).
Cuni et al., A sustained activation of P13K/NF-kappaB pathway is ciritical for the survival of chronic lymphocytic leukemia B cells, *Leukemia*, 18:1391-400 (2004).
Damle et al., B-cell chronic lymphocytic leukemia cells express a surface membrane phenotype of activated, antigen-experienced B lymphocytes, *Blood*, 99:4087-93 (2002).
Damle et al., Ig V gene mutation status and CD38 expression as novel prognostic indicators in chronic lymphocytic leukemia, *Blood*, 94:1840-7 (1999).
D'Arena et al., Prognostic significance of combined analysis of ZAP-70 and CD38 in chronic lymphocytic leukemia, *Am. J. Hematol*, 82(9):787-91 (2007).
Durig et al., ZAP-70 expression is a prognostic factor in chronic lymphocytic leukemia, *Leukemia*, 17:2426-34 (2003).
Faderl et al., Expression profile of 11 proteins and their prognostic significance in patients with chronic lymphocytic leukemia (CLL), *Leukemia*, 16:1045-52 (2002).

Furman et al., Modulation of NF-kappa B activity and apoptosis in chronic lymphocytic leukemia B cells, *J. Immunol*, 164:2200-6 (2000).
Ghia et al., The pattern of CD38 expression defines a distinct subset of chronic lymphocytic leukemia (CLL) patients at risk of disease progression, *Blood*, 101:1262-9 (2003).
Hamblin et al., CD38 expression and immunoglobulin variable region mutations are independent prognostic variables in chronic lymphocytic leukemia, but CD38 expression may vary during the course of the disease, *Blood*, 99:1023-9 (2002).
Hamblin et al., Unmutated Ig V(H) genes are associated with a more aggressive form of chronic lymphocytic leukemia, *Blood*, 94:1848-54 (1999).
Hewamana et al., The NF-KB subunit, Rel A, is associated with in vitro survival and clinical disease progression in chronic lymphocytic leukemia and represents a promising therapeutic target, *Blood*, Jan. 28, 2008; [Epub ahead of print].
Hivroz et al., Cross-linking of membrane IgM on B CLL cells: dissociation between intracellular free $Ca^{2+}$ mobilization and cell proliferation, *Eur J. Immunol.*, 18:1811-7 (1988).
Huttmann, Gene expression signatures separate B-cell chronic lymphocytic leukaemia prognostic subgroups defined by ZAP-70 and CD38 expression status, *Leukemia*, 20(10):1774-82 (2006).
Ku et al, Role and regulation of Rel/NF-kappaB activity in antiimmunoglobulin-induced apoptosis in WEHI-231 B lymphoma cells, *Cell Signal*, 12:245-53 (2000).
Lanham et al. Differential signaling via surface IgM is associated with VH gene mutational status and CD38 expression in chronic lymphocytic leukemia, *Blood*, 101:1087-93 (2003).
Montserrat, New prognostic markers in CLL, *Hematology Am. Soc. Hematol. Educ. Program*, 279-84 (2006).
Montserrat et al., Chronic lymphocytic leukemia: prognostic factors and natural history, *Baillieres Clin Haematol*, 6:849-66 (1993).
Mori et al., Bay 11-7082 inhibits transcription factor NF-kappaB and induces apoptosis of HTLVI-infected T-cell lines and primary adult T-cell leukemia cells, *Blood*, 100:1828-34 (2002).
Nedellec et al., B cell response to surface IgM cross-linking identifies different prognostic groups of B-chronic lymphocytic leukemia patients, *J Immunol*, 174:3749-56 (2005).
Patke et al., Survival signaling in resting B Cells, *Curr Opin Immunol*, 16:251-5 (2004).
Pepper et al., Highly purified $CD38^+$ and $CD38^-$ sub-clones derived from the same chronic lymphocytic leukemia patient have distinct gene expression signatures despite their monoclonal origin, *Leukemia*, 21(4):687-96 (2007).
Petlickovski et al., Sustained signaling through the B-cell receptor induces Mcl-1 and promotes survival of chronic lymphocytic leukemia B cells, *Blood*, 105:4820-7 (2005).
Rassenti et al., ZAP-70 compared with immunoglobulin heavy-chain gene mutation status as a predictor of disease progression in chronic lymphocytic leukemia, *N Engl. J. Med.*, 351:893-901 (2004).

(Continued)

*Primary Examiner*—Sean E Aeder
(74) *Attorney, Agent, or Firm*—Marshall, Gerstein & Borun LLP

(57) ABSTRACT

The invention relates to materials and methods for evaluating the prognosis of a patient presenting with chronic myelogenous leukaemia (CLL) and for CLL therapy.

5 Claims, 9 Drawing Sheets

OTHER PUBLICATIONS

Rodriguez et al., Spanish National Cancer Centre (CNIO), Molecular heterogeneity in chronic lymphocytic leukemia is dependent on BCR signlaing: clinical correlation, *Leukemia*, 21(9):1984-91 (2007).

Romano et al., CD40 and B chronic lymphocytic leukemia cell response to fludarabine: the influence of NF-KB/Rel. transcription factors on chemotherapy induced apoptosis, *Leuk. Lymphoma*, 36:255-62 (2000).

Shanafelt et al., Prognosis at diagnosis: integrating molecular biologic insights into clinical practice for patients with CLL, *Blood*, 103:1202-10 (2004).

Tian et al., Bcl10 can promote survival of antigenstimulated B lymphocytes, *Blood*, 106:2105-12 (2005).

Wierda et al., Prognostic nomogram and index for overall survival in previously untreated patients with chronic lymphocytic leukemia, *Blook*, 109(110):4679-85 (2007).

Zupo et al., CD38 expression distinguishes two group so f B-cell chronic lymphocytic leukemias with different responses to anti-IgM antibodies and propensity to apoptosis, *Blood*, 88:1365-74 (1996).

* cited by examiner

SEQUENCE LISTING

```
<160> NUMBER OF SEQ ID NOS: 7

<210> SEQ ID NO 1
<211> LENGTH: 25
<212> TYPE: DNA
<213> ORGANISM: Human

<400> SEQUENCE: 1
ggcctcagtg aaggtctcct gcaag                                          25

<210> SEQ ID NO 2
<211> LENGTH: 25
<212> TYPE: DNA
<213> ORGANISM: Human

<400> SEQUENCE: 2
gtctggtcct acgctggtga aaccc                                          25

<210> SEQ ID NO 3
<211> LENGTH: 25
<212> TYPE: DNA
<213> ORGANISM: Human

<400> SEQUENCE: 3 ctgggggtc cctgagactc tcctg                                           25

<210> SEQ ID NO 4
<211> LENGTH: 25
<212> TYPE: DNA
<213> ORGANISM: Human

<400> SEQUENCE: 4
cttcggagac cctgtccctc acctg                                          25

<210> SEQ ID NO 5
<211> LENGTH: 25
<212> TYPE: DNA
<213> ORGANISM: Human

<400> SEQUENCE: 5
cggggagtct ctgaagatct cctgt                                          25

<210> SEQ ID NO 6
<211> LENGTH: 25
<212> TYPE: DNA
<213> ORGANISM: Human
```

-continued

```
<400> SEQUENCE: 6
tcgcagaccc tctcactcac ctgtg                                              25

<210> SEQ ID NO 7
<211> LENGTH: 22
<212> TYPE: DNA
<213> ORGANISM: Human

<400> SEQUENCE: 7
ccagtggcag aggagtccat tc                                                 22
```

CHRONIC LYMPHOCYTIC LEUKAEMIA

FIELD OF THE INVENTION

The invention relates to a novel method for determining the prognosis of a patient presenting with chronic lymphocytic leukaemia; a method of treatment based upon the aforementioned prognosis; and an apparatus, including parts thereof, for performing said prognosis.

BACKGROUND

Chronic lymphocytic leukaemia (CLL) is the most common adult leukaemia in the Western World and is characterised by the accumulation of immuno-incompetent, monoclonal $CD5^+$B-lymphocytes[2]. Some patients show rapid disease progression with a mean survival of less than 36 months, whereas others exhibit a more indolent disease profile with a better prognosis. Three important laboratory prognostic markers are used to stratify patient risk: somatic mutation of immunoglobulin variable heavy chain (VH) genes, the expression of CD38 and the expression of the T-cell tyrosine kinase, ZAP-70[1,3-10]. There is evidence that different prognostic subsets of CLL cells have altered signalling properties that may contribute to disparity in clinical outcomes. Cells from CLL patients with mutated VH genes, who have a good clinical prognosis, often show a reduced response to IgM ligation of the B-cell receptor (BCR) as measured by changes in tyrosine phosphorylation[11,12]. In addition, the poor prognostic markers, CD38 and ZAP-70, have also been shown to correlate with the ability of CLL cells to signal via the BCR with high expression associated with signalling competence[13,14]. However, the interplay between the three prognostic markers and cell signalling is the subject of debate.

CLL cells with unmutated $V_H$ genes usually have higher ZAP-70 expression and, following anti-IgM ligation of the BCR, are able to activate NF-κB.[6] Indeed, ZAP-70 appears to act as an enhancer of BCR signaling[7]. NF-κB proteins are transcription factors affecting many different survival signalling pathways and play an important role in the growth, differentiation and apoptosis of normal B-lymphocytes.[8] In addition, NF-κB has been shown to be involved in the pathology of both non-haemopoietic and haemopoietic malignancies including CLL and non-Hodgkin's lymphoma.[9]

NF-κB is a collective name for a group of inducible homo- and hetero-dimeric transcription factors made up of members of the Rel family of DNA binding proteins. In humans this family is comprised of c-Rel, Rel B, p50, p52 and p65 (Rel A) which when bound in the cytoplasm to inhibitory IκB proteins are inactive.[10] Various factors including ligation of CD40 and the BCR result in proteasomal degradation of IκB releasing NF-κB which then translocates to the nucleus.[8;10] Once in the nucleus NF-κB can enhance survival by inducing anti-apoptotic proteins including IAPs, FLICE (FADD-like IL-1β-converting enzyme) and FLIP (FADD-like interleukin 1β-converting enzyme-inhibitory protein).[11-13] CLL cells have been reported to exhibit high constitutive NF-κB activation compared to normal B-lymphocytes.[14-16] Whilst the exact causes of constitutive over expression of NF-κB are not fully resolved, many factors including Akt activation, BCR signalling, CD40 ligation, IL-4 and BAFF have been shown to increase NF-κB activity and enhance CLL cell survival with members of the Bcl-2 family being important transcriptional targets.[6;17-20]

The crucial question for patients presenting with CLL is the nature of the disease progression. Clearly, patients with an aggressive form of the disease need to receive early clinical intervention. In contrast those patients with a more benign form of the disease simply need to be monitored until such time as the disease takes on a more aggressive form at which point chemotherapy can be commenced. As many will appreciate, it is inappropriate to expose someone presenting with a disease that is unlikely to be life-threatening for up to 30 years with highly dangerous chemotherapeutic drugs. An assay that is therefore able to discriminate between an aggressive form of CLL and a more benign form would be useful.

SUMMARY OF THE INVENTION

We have therefore analysed samples from 64 patients in order to quantify cellular features and intracellular changes that occur before and after anti-IgM ligation of the B-cell receptor. Significantly, we have identified a threshold for protein tyrosine phosphorylation events that triggers the activation of the transcription factor, NF-θB. Surprisingly, we have discovered that patients with protein tyrosine phosphorylation levels above a given threshold have a much shorter time to first treatment and therefore, this threshold was able to identify subsets of CLL patients with stage Binet A disease and mutated $V_H$ genes that have an unfavourable prognosis. [Binet Stage A patients have fewer than three areas of enlarged lymphoid tissue. Enlarged lymph nodes of the neck, underarms, and groin, as well as the spleen, are each considered "one group," whether unilateral (one-sided) or bilateral (on both sides). No evidence of anaemia (Haemoglobin>10 g/dL) or thrombocytopenia (platelets>$100 \times 10^3$/μl). Reference: Binet, J. L., Auquier, A., Dighiero, G., Chastang, C., Piguet, H., Goasguen, J., Vaugier, G., Potron, G., Colona, P., Oberling, F., Thomas, M., Tchernia, G., Jacquillat, C., Boivin, P., Lesty, C., Duault, M. T., Monconduit, M., Belabbes, S. and Gremy, F. A new prognostic classification of chronic lymphocytic leukemia derived from a multivariate survival analysis, Cancer, 48: 198-206, 1981.] The discrimination of this group of patients has not been previously possible and represents a significant advance.

One aspect of the invention is a method for evaluating a patient presenting with chronic lymphocytic leukaemia (CLL). In one variation, the method comprises:

calculating a CLL cell protein tyrosine phosphorylation ($PY_{PostIgM}$) from measurements of a $V_H$ gene mutation status, CD38 expression, and ZAP-70 expression in lymphocytes from the patient, wherein an elevated $PY_{PostIgM}$ correlates with a poor prognosis. The calculated $PY_{PostIgM}$ is a new and useful parameter for medical personnel to evaluate a patient's condition and make treatment decisions.

A related aspect of the invention is a method for determining the prognosis of a patient presenting with chronic lymphocytic leukaemia. Optionally, the method further includes a treatment decision/regimen, which depends on the prognosis.

In one variation, the invention is a method for determining a prognosis of a patient presenting with chronic lymphocytic leukaemia (CLL), the method comprising: calculating a CLL cell protein tyrosine phosphorylation ($PY_{PostIgM}$) from measurements of a $V_H$ gene mutation status, CD38 expression, and ZAP-70 expression in lymphocytes from the patient; and determining a prognosis of the patient from the calculation of $PY_{PostIgM}$, wherein an elevated $PY_{PostIgM}$ correlates with a poor prognosis.

In some preferred embodiments, the $PY_{PostIgM}$ calculation is a weighted sum of the measurements of a $V_H$ gene mutation status ($V_H$), CD38 expression (CD38), and ZAP-70 expression (ZAP70) in lymphocytes from the patient, according to the following weighted relationship:

$$1.96\sqrt{CD38}:0.39V_H:0.13ZAP70,$$

wherein CD38=CLL cell surface presence of CD38, expressed as % of CLL cells with greater fluorescence than an isotype-matched control;

wherein $V_H=V_H$ gene mutation status, expressed as % homology to the closest germline sequence; and wherein ZAP70=CLL cell ZAP-70 expression, expressed as % of CLL cells with equal or greater fluorescence than the T-cell population in the same sample. According to the formula, Values expressed as a % are expressed as a number between 0 and 100 (inclusive).

In order to take account of inter-laboratory and other variations in measurement, the weighted relationship is optionally expressed ±10%, or 5%, or 2%. For example, in a preferred variation, the weighted relationship is expressed as:

$$(1.96\pm0.19)\sqrt{CD38}:(0.39\pm0.03)V_H:(0.13\pm0.01)ZAP70,$$

In some highly preferred embodiments, the $PY_{PostIgM}$ calculation is according to the formula:

$$PY_{PostIgM}=(-26.95\pm2.69)+((1.96\pm0.19)\sqrt{CD38})+((0.39\pm0.03)V_H\text{status})+((0.13\pm0.01)ZAP70)$$

wherein a $PY_{PostIgM}$ calculation above 26±2.6 correlates with a conclusion that the prognosis for said patient is poor. It will be appreciated that this threshold value of 26 is specific to the particular iteration of the formula recited above, and that the formula can be manipulated (e.g., by changing the constant −26.95; or proportionally changing the factors (1.96, 0.39, 0.13)) to yield a mathematically equivalent formula with a different threshold value. All such equivalent formulas are intended to be within the scope of the invention, for all various aspects or embodiments of the invention that are described with reference to such formula. The formula also can be expressed without the ±10% variation built into the coefficients, although it should be understood that such 10% variation is considered an equivalent.

Practicing the method as described above involves a calculation based on three stated measurements, which may be measured by the same or different entity as the entity that performs the calculating, and which may be measured by one, or two, or three different entities. In one variation, the method for determining the prognosis of the patient further comprises steps, prior to said calculating step, of determining the mutation status of $V_H$ gene relative to a wildtype $V_H$ gene sequence in lymphocytes from the patient; determining the expression of CD38 on the surface of CLL cells from the patient relative to an isotype matched control; and determining the expression of ZAP-70 in CLL cells of the patient, relative to ZAP-70 expression in lymphocytes of the patient. In a preferred variation, the method further comprising a step, prior to the determining steps, of isolating lymphocytes from said patient, which are used to obtain the measurements.

In a related variation, the invention is a method for determining the prognosis of a patient presenting with chronic lymphocytic leukaemia, comprising:

a) isolating a population of lymphocytes from a blood sample taken from said patient;

b) examining the DNA of said lymphocytes in order to determine the mutation status of $V_H$ gene;

c) determining the expression of CD38;

d) determining the expression of ZAP-70; and e) feeding the information from steps b), c) and d) into the following equation in order to determine the protein tyrosine phosphorylation of said lymphocytes:

$$PY_{PostIgM}=(-26.95\pm2.69)+((1.96\pm0.19)\sqrt{CD38})+((0.39\pm0.03)V_H\text{status})+((0.13\pm0.01)ZAP70)$$

where:

$PY_{PostIgM}$=CLL cell protein tyrosine phosphorylation (following IgM stimulation);

CD38=CLL cell surface presence of CD38, expressed as a %; Percentage in this context means the percentage of CLL cells with greater fluorescence than the isotype-matched control.

$V_H$ status=$V_H$ gene mutation status, expressed as a % homology to the closet germline sequence; and ZAP-70=CLL cell ZAP-70 expression, expressed as a %. Percentage in this context means the percentage of CLL cells with equal or greater fluorescence than the T-cell population in the same sample.

and, where said protein tyrosine phosphorylation is above a certain threshold, concluding that the prognosis for said patient is poor.

In a preferred method of the invention the threshold is 26±2.6.

Alternatively, given that the methodology involves the expression of a relationship in mathematical terms the threshold could be stated to be where $$((1.96\pm0.19)\sqrt{CD38})+((0.39\pm0.03)V_H\text{status})+((0.13\pm0.01)ZAP70)$$

is equal or greater than 50 and more preferably 52.95.

In order to take account of inter-laboratory variation, the figures quoted in the above equation are ±10%. The equation also can be expressed without the ±10% expression.

In a preferred method of the invention part c) above involves quantifying the amount of CD38 on the surface of said lymphocytes.

In a related embodiment, the invention is a method for treating an individual/patient with CLL based on the prognosis determined according to a method of the invention. If the prognosis is poor, then the treatment comprises administering an approved anticancer therapeutic such as those described in greater detail below. If the PY measurement is below the threshold and the prognosis is therefore good (not poor), then the treating may be, e.g., refraining from anticancer therapeutics and prescribing healthy lifestyle regimens and re-evaluating prognosis in a number of months or years (e.g., any period ranging from one month to five years, such as 1 month, 2, 3, 4, 6, 8, 9, 12 months, 2, 3, or 4 years).

According to a related aspect of the invention, there is provided a method for treating an individual presenting with chronic lymphocytic leukaemia comprising:

a) isolating a population of lymphocytes from a blood sample taken from said patient;

b) examining the DNA of said lymphocytes in order to determine the mutation status of $V_H$ gene;

c) determining the expression of CD38;

d) determining the expression of ZAP-70; and e) feeding the information from steps b), c) and d) into the following equation in order to determine the protein tyrosine phosphorylation of said lymphocytes:

$$PY_{PostIgM} = (-26.95 \pm 2.69) + ((1.96 \pm 0.19)\sqrt{CD38}) + ((0.39 \pm 0.03)V_H\text{status}) + ((0.13 \pm 0.01)ZAP70)$$

where:

$PY_{PostIgM}$=CLL cell protein tyrosine phosphorylation (following IgM stimulation);

CD38=CLL cell surface presence of CD38, expressed as a %. Percentage in this context means the percentage of CLL cells with greater fluorescence than the isotype-matched control.

$V_H$ status=$V_H$ gene mutation status, expressed as a % homology to the closest germline sequence; and ZAP-70=CLL cell ZAP-70 expression, expressed as a %. Percentage in this context means the percentage of CLL cells with equal or greater fluorescence than the T-cell population in the same sample;

and, where said protein tyrosine phosphorylation is above a certain threshold, concluding that the prognosis for said patient is poor and so prescribing immediate treatment to combat the disease.

In a preferred method of the invention the said threshold is 26±2.6.

Alternatively, given that the methodology involves the expression of a relationship in mathematical terms, the threshold could be stated to be where $$((1.96 \pm 0.19)\sqrt{CD38}) + ((0.39 \pm 0.03)V_H\text{status}) + ((0.13 \pm 0.01)ZAP70)$$

is equal or greater than 50 and more preferably 52.95.

In order to take account of inter-laboratory variation, the figures quoted in the above equation are ±10%;

In a preferred method of the invention part c) above involves quantifying the amount of CD38 on the surface of said lymphocytes.

The invention also includes materials, devices, apparatuses, and the like that are useful for carrying out methods of the invention.

For example, in one embodiment, the invention is a computer readable medium having computer executable instructions for determining a prognosis of a patient presenting with chronic lymphocytic leukaemia (CLL), the computer readable medium comprising:

a routine stored on the computer readable medium and adapted to be executed by a processor to receive input values for measurements of a $V_H$ gene mutation status ($V_H$), CD38 expression (CD38), and ZAP-70 expression (ZAP70) obtained from lymphocytes of a human with chronic lymphcytic leukemia (CLL); and a routine stored on the computer readable medium and adapted to be executed by a processor to generate a CLL cell protein tyrosine phosphorylation ($PY_{PostIgM}$) from said measurements. In some preferred embodiments, the computer readable medium further comprises a routine stored on the computer readable medium and adapted to be executed by a processor to calculate the $PY_{PostIgM}$ as a sum based on the measurements according to the following weighted relationship:

$$(1.96 \pm 0.19)\sqrt{CD38} : (0.39 \pm 0.03)V_H : (0.13 \pm 0.01)ZAP70,$$

wherein CD38=CLL cell surface presence of CD38, expressed as % of CLL cells with greater fluorescence than an isotype-matched control;

wherein $V_H$ status=$V_H$ gene mutation status, expressed as % homology to the closest germline sequence; and wherein ZAP70=CLL cell ZAP-70 expression, expressed as % of CLL cells with equal or greater fluorescence than the T-cell population in the same sample.

In some highly preferred embodiments, the routine which calculates the $PY_{PostIgM}$ comprises a routine stored on the computer readable medium and adapted to be executed by a processor to calculate the $PY_{PostIgM}$ according to the following formula:

$$PY_{PostIgM} = (-26.95 \pm 2.69) + ((1.96 \pm 0.19)\sqrt{CD38}) + ((0.39 \pm 0.03)V_H\text{status}) + ((0.13 \pm 0.01)ZAP70).$$

In some variations, the computer readable medium as described in the preceding paragraphs further comprises a routine stored on the computer readable medium and adapted to be executed by a processor to generate a prognosis for the human with CLL based on the $PY_{PostIgM}$, wherein an elevated $PY_{PostIgM}$ correlates with a poor prognosis. A $PY_{PostIgM}$ that is not elevated is not scored as a poor prognosis, but rather as a good prognosis.

In still other variations, the computer readable medium further comprises a routine stored on the computer readable medium and adapted to be executed by a processor to generate a course of treatment for the human based on the $PY_{PostIgM}$ or based on the prognosis.

Another embodiment of the invention is a system for generating a medical prognosis in a human subject with chronic lymphocytic leukemia, the system comprising:

a processor;

a display operatively coupled to the processor;

a routine adapted to be executed by the processor to receive input values for measurements of a $V_H$ gene mutation status ($V_H$), CD38 expression (CD38), and ZAP-70 expression (ZAP70) obtained from lymphocytes of a human with chronic lymphcytic leukemia (CLL);

a routine adapted to be executed by the processor to generate a CLL cell protein tyrosine phosphorylation ($PY_{PostIgM}$) from the measurements; and a routine adapted to be executed by the processor to display a representation of the $PY_{PostIgM}$. In preferred embodiments, the system further comprises a routine adapted to be executed by the processor to calculate the $PY_{PostIgM}$ as a sum based on the measurements according to the following weighted relationship:

$$(1.96 \pm 0.19)\sqrt{CD38} : (0.39 \pm 0.03)V_H : (0.13 \pm 0.01)ZAP70$$

wherein CD38=CLL cell surface presence of CD38, expressed as % of CLL cells with greater fluorescence than an isotype-matched control;

wherein $V_H$ status=$V_H$ gene mutation status, expressed as % homology to the closest germline sequence; and wherein ZAP70=CLL cell ZAP-70 expression, expressed as % of CLL cells with equal or greater fluorescence than the T-cell population in the same sample.

In some highly preferred embodiments, the system further comprises a routine adapted to be executed by the processor to calculate the $PY_{PostIgM}$ according to the following formula:

$$PY_{PostIgM} = (-26.95 \pm 2.69) + ((1.96 \pm 0.19)\sqrt{CD38}) + ((0.39 \pm 0.03)V_H\text{status}) + ((0.13 \pm 0.01)ZAP70)$$

In some variations of the invention, the system further comprises a routine adapted to be executed by the processor to generate a prognosis for the human with CLL based on the $PY_{PostIgM}$. In some variations the system further comprises a routine adapted to be executed by the processor to generate a course of treatment for the human based on the $PY_{PostIgM}$ or based on the prognosis. The system preferably includes one or more routines adopted to be executed by the processor to display a representation of the prognosis and/or a representation of the course of treatment.

According to a further aspect of the invention there is provided an apparatus for determining the prognosis of a patient presenting with chronic lymphocytic leukaemia comprising:

means for receiving information concerning the $V_H$ gene status of an individual;

means for receiving information concerning the expression of CD38 in CLL cells taken from said patient;

means for receiving information concerning the expression ZAP-70 in CLL cells taken from said patient;

means for performing the following calculation:

$$PY_{PostIgM} = (-26.95 \pm 2.69) + ((1.96 \pm 0.19)\sqrt{CD38}) + ((0.39 \pm 0.03)V_H\text{status}) + ((0.13 \pm 0.01)\text{ZAP70})$$

[where:

$PY_{PostIgM}$=CLL cell protein tyrosine phosphorylation (following IgM stimulation);

CD38=CLL cell surface presence of CD38, expressed as a %; Percentage in this context means the percentage of CLL cells with greater fluorescence than the isotype-matched control.

$V_H$ status=$V_H$ gene mutation status, expressed as a % homology to the closest germline sequence; and ZAP-70=CLL cell ZAP-70 expression, expressed as a %. Percentage in this context means the percentage of CLL cells with equal or greater fluorescence than the T-cell population in the same sample.]

means for determining whether the phosphorylation status is above or below a certain threshold;

means for indicating that the prognosis of the patient is poor where the phosphorylation status is above the threshold; and means for indicating that the prognosis for the patient is good where the phosphorylation status is below the threshold.

In a preferred apparatus or computer system of the invention set forth above, the threshold is 26±2.6.

Alternatively, given that the above calculation involves the expression of a relationship in mathematical terms the said threshold could be stated to be where $$((1.96 \pm 0.19)\sqrt{CD38}) + ((0.39 \pm 0.03)V_H\text{status}) + ((0.13 \pm 0.01)\text{ZAP70})$$

is equal or greater than 50 and more preferably 52.95.

In order to take account of inter-laboratory variation, the figures quoted in the above equation are ±10%;

According to a further aspect of the invention there is provided a computer readable medium having computer executable instructions for determining the prognosis of a patient presenting with chronic lymphocytic leukaemia comprising:

a routine stored on the computer readable medium and adapted to be executed by a processor to perform the following calculation:

$$PY_{PostIgM} = (-26.95 \pm 2.69) + ((1.96 \pm 0.19)\sqrt{CD38}) + ((0.39 \pm 0.03)V_H\text{status}) + ((0.13 \pm 0.01)\text{ZAP70})$$

where:

$PY_{PostIgM}$=CLL cell protein tyrosine phosphorylation (following IgM stimulation);

CD38=CLL cell surface presence of CD38, expressed as a %; Percentage in this context means the percentage of CLL cells with greater fluorescence than the isotype-matched control.

$V_H$ status=$V_H$ gene mutation status, expressed as a % homology to the closest germline sequence; and ZAP-70=CLL cell ZAP-70 expression, expressed as a %. Percentage in this context means the percentage of CLL cells with equal or greater fluorescence than the T-cell population in the same sample.];

a routine stored on the computer readable medium and adapted to be executed by a processor to determine whether the phosphorylation status is above or below a certain threshold;

a routine stored on the computer readable medium and adapted to be executed by a processor to provide an indication that the prognosis of the patient is poor if the phosphorylation status is above the threshold; and a routine stored on the computer readable medium adapted to be executed by a processor to provide an indication that the prognosis for the patient is good if the phosphorylation status is below the threshold.

In a preferred product of the invention the threshold is 26±2.6.

Alternatively, given that the above threshold involves the expression of a relationship in mathematical terms the said threshold could be stated to be where $$((1.96 \pm 0.19)\sqrt{CD38}) + ((0.39 \pm 0.03)V_H\text{status}) + ((0.13 \pm 0.01)\text{ZAP70})$$

is equal or greater than 50 and more preferably 52.95.

In order to take account of inter-laboratory variation, the figures quoted in the above equation are ±10%.

Those skilled in the art will appreciate that methods undertaken for the isolation of lymphocytes and also for determining the $V_H$ gene mutation status within lymphocytes; the measurement of CD38 on the surface of lymphocytes and also the expression of ZAP-70 are well known to those skilled in the art. Indeed, standard operating practices exist for each of these methods. However, invention lies in the combination of these techniques for generating the aforementioned prognosis and also for undertaking the aforementioned treatment. Moreover, invention also lies in the realisation that a relationship exists between these three factors and that this relationship, surprisingly, can be resolved to a determination of the protein tyrosine phosphorylation within CLL cells; above a certain threshold, this phosphorylation is an indicator for a poor prognosis; whilst, conversely, below said threshold this indicator is indicativor of a good prognosis.

Significantly, therefore, we now have a means of determining which patients presenting with chronic lymphocytic leukaemia will require treatment and those which will simply require monitoring. Those who require monitoring can be regularly tested, as described above, in order to determine whether the protein tyrosine phosphorylation level within CLL cells has changed and, at the point of change, those individuals can then be subjected to treatment.

Typically, for patients requiring therapy, the standard first line therapy for chronic lymphocytic leukaemia in the UK is combination chemotherapy using fludarabine and cyclophosphamide. In the US rituximab is added to the fludarabine/cyclophosphamide combination. Alternative therapies include chlorambucil monotherapy, pentostatin/cyclophosphamide/rituximab combination therapy, alemtuzumab, rituximab maintenance therapy and cyclophosphamide, adriamycin, vincristine and prednisolone (CHOP therapy). In Europe some countries prefer to use cladribine. All varieties of chemotherapies, biologics, or other agents for cancer treatment are contemplated.

In addition to the foregoing, the invention includes, as an additional aspect, all embodiments of the invention narrower in scope in any way than the variations specifically mentioned above. For example, although aspects of the invention may have been described by reference to a genus or a range of values for brevity, it should be understood that each member of the genus and each value within the range is intended as an aspect of the invention. Likewise, various aspects and features of the invention can be combined, creating additional aspects which are intended to be within the scope of the invention. Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

BRIEF DESCRIPTION OF THE DRAWING

The invention will now be exemplified by way of example only with reference to the following methods and figures wherein:

FIG. 4 shows the gating of a FACS Calibur flow cytometer.

DETAILED DESCRIPTION

Figure 1A:
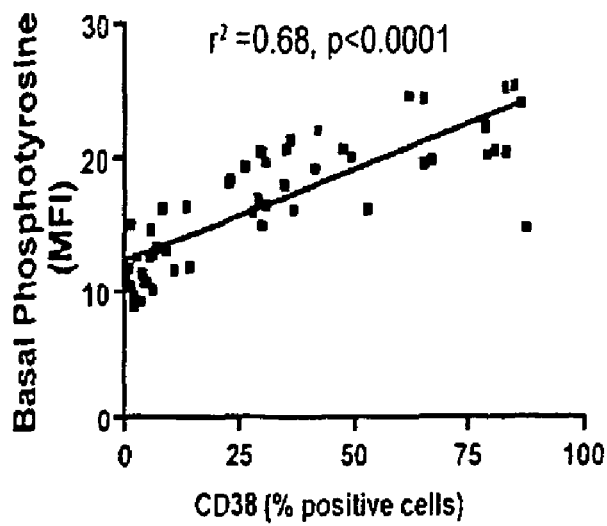
FIG. 1 shows protein tyrosine phosphorylation can be explained as a function of three of the prognostic markers of chronic lymphocytic leukaemia (FIG. 1A). Basal phosphotyrosine correlates with the expression of the cell surface marker CD38. The change in phosphotyrosine induced following treatment with IgM (conc) was expressed as a function of $V_H$ status (FIG. 1B) or the expression of ZAP-70 (FIG. 1C). Phosphotyrosine, post IgM treatment, was calculated using an equation that depends on CD38, $V_H$ status and the expression of ZAP-70 and shows a correlation coefficient of 0.808 showing that we can explain more than 80% of the variation in cellular phosphotyrosine as a function of these three markers (FIG. 1D)

Isolation of Mononuclear Cells from Whole Blood

Principle

Lymphocytes can be isolated from whole blood by density centrifugation using Histopaque-1077 (Sigma). This is a polysucrose (5.7 g/dl) and sodium diatrizoate (9.0 g/dl) solution which is adjusted to a density gradient 1.077 g/cm³ and facilitates the sedimentation of erythrocytes and granulocytes whilst trapping mononuclear cells (including lymphocytes) at the plasma-Histopaque interface.

Method

1. Remove a 3.0 ml aliquot of Histopaque-1077 from the fridge (in a 15 ml conical tube) and equilibrate to room temperature.

2. Carefully layer up to 8.0 ml of whole blood onto the Histopaque, close the screw cap and then centrifuge at 400×g (1500 rpm) for 30 mins.

3. Remove tube from centrifuge and carefully remove the upper layer to within 0.5 cm of the opaque interface using a Pasteur pipette and discard.

4. Transfer the opaque interface (containing the mononuclear cells) with a sterile Pasteur pipette into a sterile 15 ml conical tube.

5. Add 10 ml of sterile phosphate buffered saline to the cell suspension and mix by gentle aspiration.

6. Centrifuge the tube at 300×g (1200 rpm) for 10 mins, aspirate the supernatant and discard.

7. Add 10 ml of 0.87% w/v of ammonium chloride solution to lyse contaminating red cells. Gently aspirate and leave at room temperature for 5 mins.

8. Centrifuge the tube at 300×g (1200 rpm) for 10 mins, aspirate the supernatant and discard.

9. Repeat steps 5 and 6 twice.

Determination of $V_H$ Gene Mutation Status

Principle

A number of studies have demonstrated the importance of $V_H$ gene mutation status as a prognostic marker in CLL.(1-4) The underlying biological rationale for this is controversial but is likely to be related to the fundamental biological differences between cells that have or have not undergone somatic hypermutation in response to antigen.

Method

1. Lymphocytes should be isolated as described above and aliquoted ($2\times10^6$ cells) and frozen ($-70°$ C.) until DNA extraction can be performed.

DNA Extraction

2. DNA was extracted using QIAamp DNA blood midi kit. In a 15 ml centrifuge tube, $2\times10^6$ peripheral blood mononuclear cells were added to 200 µl of QIAGEN protease.

3. To this 2.4 ml of Buffer AL was added and the solution was mixed thoroughly by vortexing. The solution was incubated at 70° C. for 10 minutes.

4. Ethanol (2 ml) was added to the sample and mixed by vortexing. Half the solution was added to the QIAamp midi column and this was centrifuged at 1850×g for 3 minutes.

5. The flow-through was discarded, and the rest of the solution was added to the column which was spun at 1850×g for 3 minutes. The filtrate was discarded. 2 ml of Buffer AW1 was added to the QIAamp midi column and this was centrifuged at 4500×g for 1 minute.

6. 2 ml of Buffer AW2 was then added to the QIAamp midi column and this was centrifuged at 4500×g for 15 minutes.

7. The flow-through and collection tube was discarded and the QIAamp midi column was placed in a fresh 15 ml centrifuge tube. 300 µl of Buffer AE was pipetted directly onto the membrane of the QIAamp midi column, and with the cap closed, it was incubated at room temperature for 5 minutes and then centrifuged for 5 minutes at 4500×g.

8. To obtain maximum DNA concentration, 300 µl of eluate containing the DNA was reloaded onto the QIAamp midi column and was incubated at room temperature for 5 minutes. It was then centrifuged at 4500×g for 5 minutes. The DNA was kept for further down stream assays such as polymerase chain reaction.

Polymerase Chain Reaction (PCR)

The DNA previously extracted was then used in a multiplexed PCR reaction with the BIOMED-2 primers.

```
                                      (SEQ ID NO: 1)
V_H1-FRI       5' GGCCTCAGTGAAGGTCTCCTGCAAG 3'

(SEQ ID NO: 2)
V_H2-FRI       5' GTCTGGTCCTACGCTGGTGAAACCC 3'

(SEQ ID NO: 3)
V_H3-FRI       5' CTGGGGGGTCCCTGAGACTCTCCTG 3'

(SEQ ID NO: 4)
V_H4-FRI       5' CTTCGGAGACCCTGTCCCTCACCTG 3'

(SEQ ID NO: 5)
V_H5-FRI       5' CGGGGAGTCTCTGAAGATCTCCTGT 3'

(SEQ ID NO: 6)
V_H6-FRI       5' TCGCAGACCCTCTCACTCACCTGTG 3'

(SEQ ID NO: 7)
J_H consensus  5' CCAGTGGCAGAGGAGTCCATTC 3'
```

9. A 5 µl solution was made up of 0.5 µg of DNA sample, 10 pmol of each primer, 2 nM of dNTPs (deoxy nucleotide triphosphates), 1 U AmpliTaq Gold and 10×PCR buffer II.

10. The DNA Thermo Cycler (ABI) was used as follows: denaturation at 94° C. for 15 minutes; 35 cycles of 94° C. for 30 seconds, 58° C. for 30 seconds and 72° C. for 30 seconds; and a final cycle of 10 minutes at 72° C.

Analysis

11. The PCR products were analysed on the Agilent bioanalyzer. The products were then sequenced directly using 3' $J_H$ consensus primer in an automated ABI Prism 3100 genetic analyser using Big-Dye terminators.

12. Comparison of the derived sample sequence was made with germline sequences stored on the Ig Blast database (http://www.ncbi.nlm.nih.gov/igblast/) and the percentage sequence homology to the closest germline sequence was determined. The highest percentage homology (expressed as a number between 0 and 100 for 100% homology) was used for subsequent calculations. Both the percentage sequence homology and the $V_H$ gene segment usage for each patient sample was noted.

Measurement of CD38 on the Surface of CLL Cells

Principle

A number of studies have shown that the quantification of CD38 on the surface of CLL cells can be a useful prognostic tool in this condition.(1-3) A triple-colour flow cytometry assay allows the positive identification of malignant CLL cells and the simultaneous analysis of CD38 expression.

Method

1. Lymphocytes should be isolated as described above 1 and aliquoted into 5 ml Falcon tubes ($1\times10^6$ cells/tubes)

2. To one aliquot of cells the following antibodies are added: 5 µl of CD5 fluorescein isothiocyante (FITC) conjugated antibody, 4 µl of CD38 R-phycoerythrin (PE) conjugated antibody and 4 µl of CD19 Allophycocyanin (APC) conjugated antibody.

3. Add the same volumes of isotype-matched control antibodies conjugated to the same fluorochromes to a separate aliquot of cells.

4. Incubated the tubes at room temperature (in the dark) for 15 mins.

5. Add 3 ml of phosphate buffered saline to each tube and centrifuge the tubes at 300×g (1200 rpm) for 10 mins, aspirate the supernatant and discard.

6. Resuspend the cell pellet in 0.5 ml of a 1% w/v paraformaldehyde solution and store in the fridge ready for flow cytometric analysis 7. The FACS Calibur flow cytometer has a template document (named "CD38 acquisition"), this should be utilised and 10,000 events acquired.

8. Analysis is performed by gating the viable lymphocytes (using forward scatter and side scatter characteristics). This gate is then applied to a CD5/CD19 dotplot and a second gate drawn around the CD5/CD19 double positive lymphocytes. This gate is finally applied to a CD38/CD19 plot and the percentage of CD38 positive CLL cells is quantified using a quadrant defined by the isotype-matched control plot of CD38/CD19 as shown in FIGS. 4A, 4B, 4C and 4D. The percentage (expressed as a number between 0 and 100) is used for subsequent calculations.

Detection of ZAP-70 by Flow Cytometry

Principle

Cells are first fixed to preserve antigens in their natural configuration and to prevent leakage of intracellular proteins across the cell membrane. Cells are then permeabilised to give antibodies access to intracellular antigens whilst leaving the morphological characteristics of the cell largely intact. This method is currently used to determine a wide range of protein expression including members of the Bcl-2 family, phopsho-specific proteins and cyclins.

Method

1. Isolate mononuclear cells from whole blood using Histopaque 1077 (see above).

2. Adjust the concentration of the isolated mononuclear cells to $1 \times 10^7$ cells/ml using PBS as a diluent (See SOP 1). Then aliquot 100 µl of this solution to the desired number of 5 ml Falcon tubes.

3. Add 5 µl of CD5-PE and 4 µl of CD19-APC to one tube and the same volumes of isotype-matched control reagents to another. Briefly vortex tubes and incubate for 10 mins at room temperature in the dark.

4. Wash cells in approximately 2 ml of PBS and then centrifuge for 5 mins at 300×g. Remove supernatant and discard.

5. Add 60 µl of Reagent A (fixative) to all tubes and incubate for 10 mins at room temperature in the dark. Wash in PBS and centrifuge as described in step 4.

6. Add 60 µl of Reagent B (permeabilisation) to the cell pellet followed by 4 µl of anti ZAP-70-Alexa fluor 488 or the same volume of the isotype-matched control reagent. Vortex tubes for 1-2 secs and incubate for 10 mins at room temperature in the dark.

7. Wash in PBS and centrifuge as described in step 4. Discard supernatant and resuspend pellet in 0.5 ml 1% paraformaldehyde in PBS. Store tubes in the fridge until analysis by flow cytometry. (1, 2).

Calculation of Post-IgM Phosphotyrosine

Principle

Figure 1B:
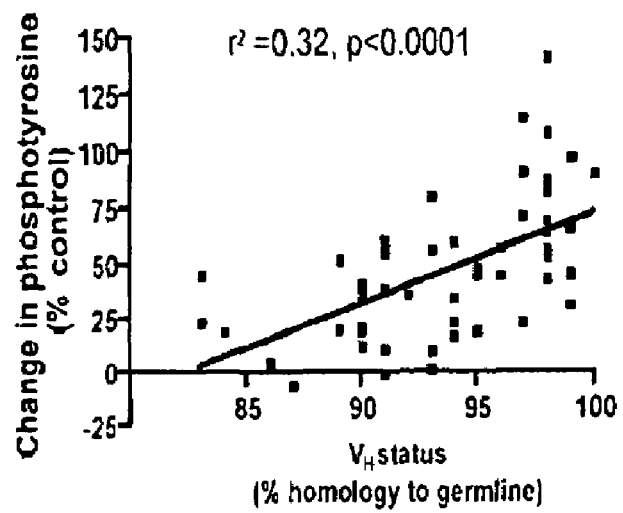
Figure 1C:
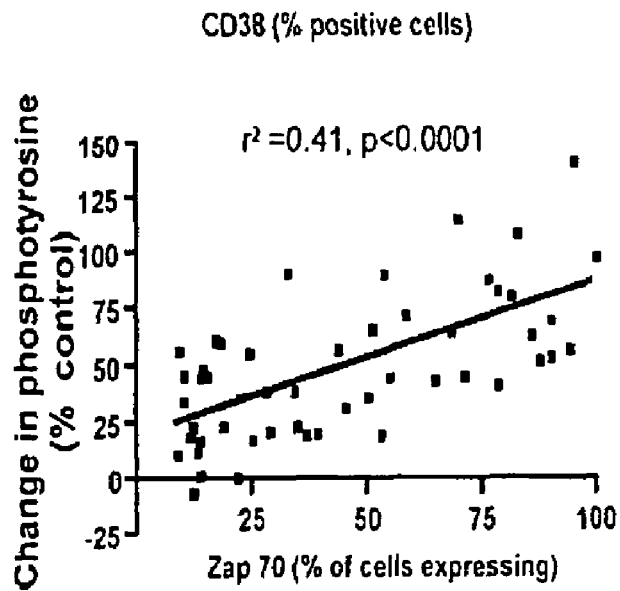
Figure 1D:
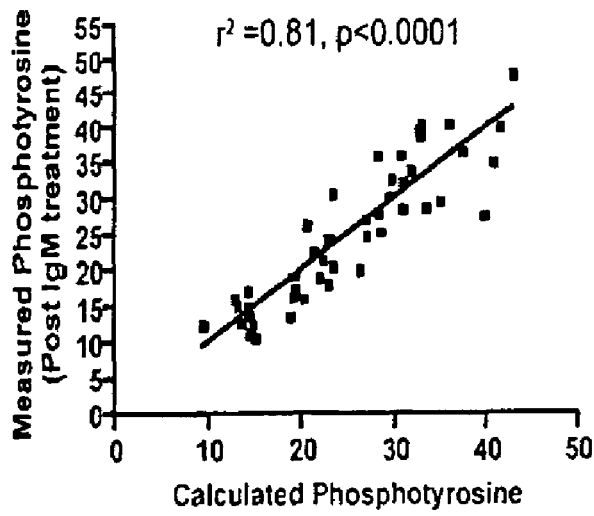

Our work clearly demonstrates that cellular protein tyrosine phosphorylation integrates $V_H$ gene mutation status, CD38 and ZAP-70 expression in an additive fashion. CD38 expression correlated with basal protein tyrosine phosphorylation (FIG. 1A) (linear regression $r^2=0.68$, $p<0.0001$), whereas $V_H$ gene mutation status (FIG. 1B) (linear regression $r^2=0.32$, $p<0.0001$) and ZAP-70 expression (FIG. 1C) (linear regression $r^2=0.41$, $p<0.0001$) correlated with the tyrosine phosphorylation induced following BCR stimulation. CD38 expression did not significantly affect the change in tyrosine phosphorylation induced following BCR stimulation suggesting an independent role for this molecule in CLL cell signaling. Our model explained 81% of the variation in protein tyrosine phosphorylation, following IgM stimulation, as a function of $V_H$ gene mutation status, and the expression of CD38 and ZAP-70 (FIG. 1D) using the following equation:

$$PY_{PostIgM} = (-26.95 \pm 2.69) + ((1.96 \pm 019)\sqrt{CD38}) + ((0.39 \pm 0.03)V_H\text{status}) + ((0.13 \pm 0.01)ZAP70)$$

[where:

$PY_{PostIgM}$=CLL cell protein tyrosine phosphorylation (following IgM stimulation);

CD38=CLL cell surface presence of CD38, expressed as a %; Percentage in this context means the percentage of CLL cells with greater fluorescence than the isotype-matched control.

$V_H$ status=$V_H$ gene mutation status, expressed as a % homology to the closest germline sequence; and ZAP-70=CLL cell ZAP-70 expression, expressed as a %. Percentage in this context means the percentage of CLL cells with equal or greater fluorescence than the T-cell population in the same sample.]

In order to take account of inter-laboratory variation, the figures quoted in the above equation are ±10%.

Method

1. Take the percentage values generated using the three methods described above. Note that all three measurements are required.

2. Calculated phosphotyrosine post IgM ($PY_{Post\ IgM}$) using the following equation:

$$PY_{PostIgM} = (-26.95 \pm 2.69) + ((1.96 \pm 0.19)\sqrt{CD38}) + ((0.39 \pm 0.03)V_H\text{status}) + ((0.13 \pm 0.01)ZAP70)$$

3. Our data shows that a calculated phosphotyrosine post IgM greater than 26±2.6 identifies a patient that will have a shorter time to first treatment.

Additional Description of the Invention

An investigation of various data transformations showed that a square root transformation of CD38 expression showed a superior correlation with basal protein tyrosine phosphorylation than the linear data model. It is noteworthy that protein tyrosine phosphorylation measurements retained significance when the patient cohort was categorized by $V_H$ status, CD38 expression or ZAP-70 expression.

Figure 2A:
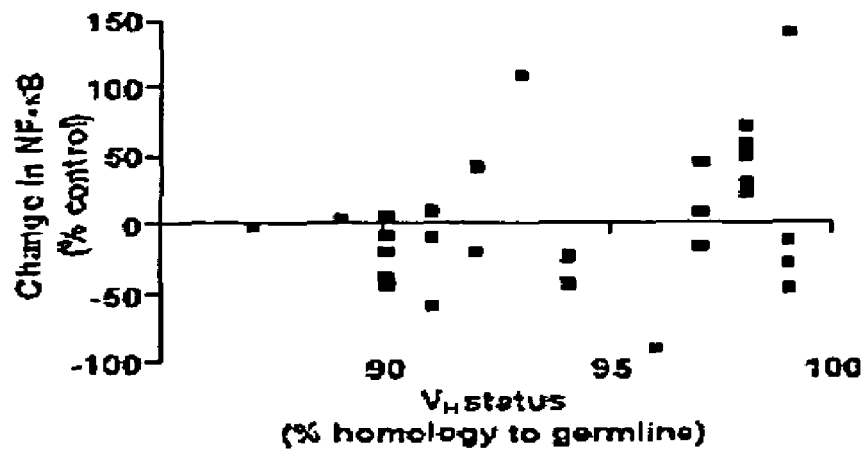
FIG. 2 shows positive and negative signals through the BCR regulate NF-κB and cell survival (FIG. 2A). IgM treatment can both increase and decrease NF-κB activity in CLL patient samples irrespective of $V_H$ status (FIG. 2B). The expression of ZAP-70 shows a positive correlation with NF-κB activation in CLL samples (FIG. 2C). Increased phosphotyrosine, post IgM treatment, causes increased NF-κB activity supporting a strength of signal hypothesis (FIG. 2D). Sample data from two patient samples. One shows an activation of NF-κB following IgM treatment for 15 minutes, compared to untreated (UT), followed by a corresponding increase in cell survival measured after 24 hours. The other patient shows the opposite phenomenon with a repression of NF-κB and an induction in cell apoptosis following IgM treatment (FIG. 2E). Increased phosphotyrosine has a reverse correlation with cell apoptosis (FIG. 2F). Variation in NF-κB can explain more than 67% of the variation in the change in cell apoptosis when both are expressed relative to their control levels.
Figure 2B:
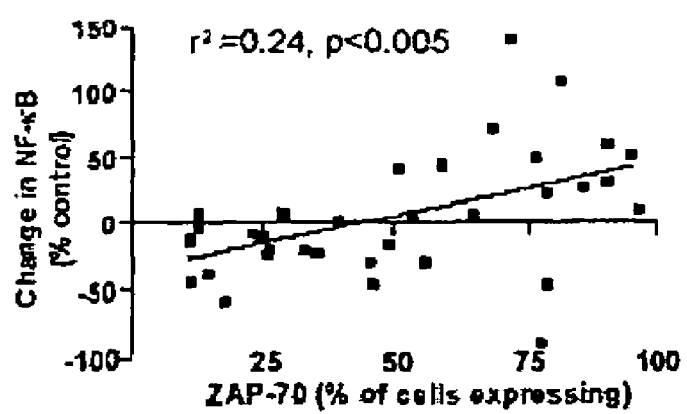
Figure 2C:
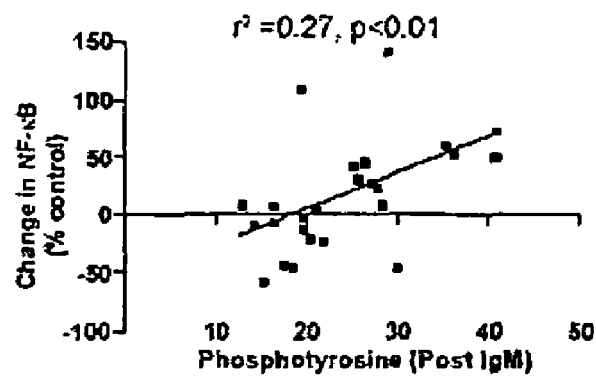
Figure 2D:
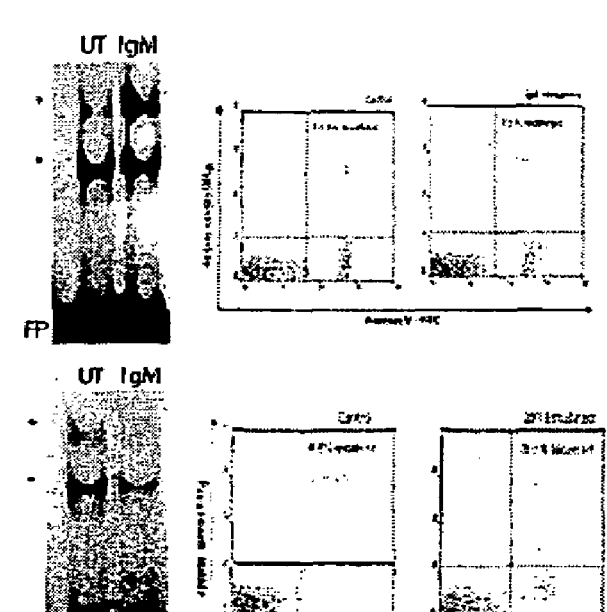

Cell signaling often results in a change in gene expression mediated by altered transcription factor activity in the nucleus of the lymphocyte. The transcription factor, NF-κB, has been reported to be elevated in CLL samples[15,16] and has been implicated in lymphocyte cell survival[17-19]. However, the regulation of NF-κB by BCR signaling is poorly characterized in CLL. Therefore, we analysed NF-κB in CLL samples using an electrophoretic mobility shift assay, before and after BCR ligation with anti-IgM (n=35). Our analysis revealed a surprising feature of CLL B-cells: BCR stimulation had the capacity to not only activate NF-κB but also to repress it in distinct patient samples. Stimulation with IgM only increased NF-κB DNA-binding in half the patient samples while in the other half of the CLL samples, stimulation through IgM resulted in a decrease in NF-κB DNA-binding (FIGS. 2A and 2D). This negative and positive signalling was independent of $V_H$ gene mutation status (FIG. 2A, no significant correlation) that is thought to define the ability of CLL cells to signal through the BCR. Negative signalling through antigen receptors has been observed in mouse model systems, most notably the induction of apoptosis by BCR stimulation of WEHI-231, a murine B-cell lymphoma line of immature phenotype[20,21]. However, CLL cells are the first human pathology where repression of NF-κB by antigen receptor stimulation has been observed.

Quantification and statistical analysis demonstrated that NF-κB activation correlated with ZAP-70 expression (FIG. 2B; linear regression $r^2=0.24$, p 0.005) but not with CD38 expression. When we considered the link between protein tyrosine phosphorylation and NF-κB activation, the change in phosphotyrosine, stimulated by IgM, showed a correlation (linear regression $r^2=0.2$, $p<0.05$,) with a more significant correlation between the levels of phosphotyrosine, post IgM treatment, and NF-κB activation (FIG. 2C; linear regression $r^2=0.27$, $p<0.01$). FIG. 2C shows a threshold of protein tyrosine phosphorylation that must be reached in order to trigger an induction of NF-κB activation (corresponding to a total phosphotyrosine MFI of 25 in these experiments). Above this threshold, eleven of twelve samples gave an induction of NF-κB, while below this value IgM stimulation repressed NF-κB in ten out of thirteen samples.

Figure 2E:
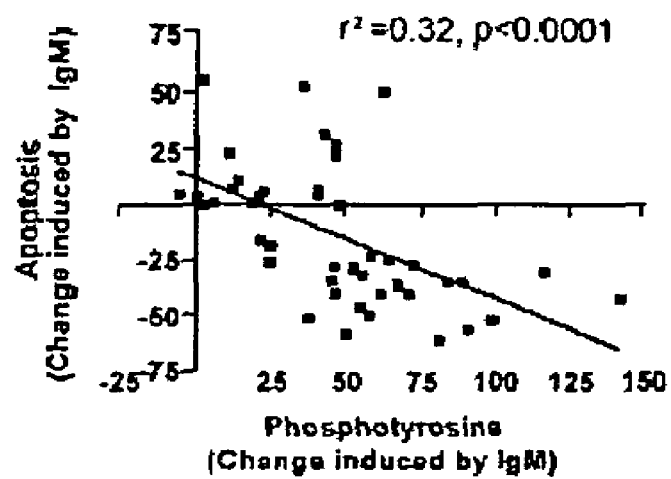

CLL is characterised by the accumulation of B-lymphocytes and so is primarily regarded as a defect in cellular apoptosis[6]. For this reason, we measured apoptosis in CLL samples with and without stimulation of the BCR with anti-IgM. As has been previously reported[22], anti-IgM treatment induced apoptosis in some CLL cells but protected others from spontaneous cell death. Interestingly, our analysis of spontaneous apoptosis revealed no significant correlation between spontaneous cell death and any variable we measured. However, levels of cellular apoptosis post IgM treatment showed an inverse correlation with the expression of CD38 and ZAP-70 although these associations had quite small correlation coefficients. More convincingly, our data showed that the change in phosphotyrosine signal can explain 32% of the variation in the change in cellular apoptosis induced by anti-IgM (FIG. 2E).

Figure 2F:
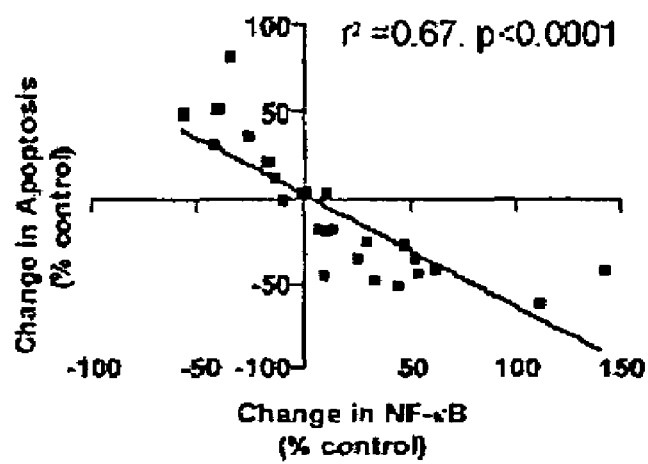

The largest correlation coefficient was observed when graphing the change in apoptosis induced by anti-IgM against the change in NF-κB activity induced by anti-IgM ($r^2=0.67$, $p<0.0001$; FIG. 2F). Thus, this correlation explains 67% of the variation in cell survival post anti-IgM treatment. As examples, FIG. 2D shows two samples, one where NF-κB was increased and so was cell survival and another where NFκ-B was decreased and there was a corresponding decrease in cell survival. Importantly, this shows that the repression of NF-κB by anti-IgM, i.e. negative signaling through the BCR, has functional relevance in terms of regulating cellular phenotype. We also used an NFκ-B inhibitor and investigated its effects on CLL cells. Treating CLL cells with Bay 11-7082[23] for 24 hours caused a dose-dependent increase in CLL cell apoptosis. This shows a causative relationship, between NF-κB and CLL cell survival, strongly supporting the correlation we observed.

Figure 3A:
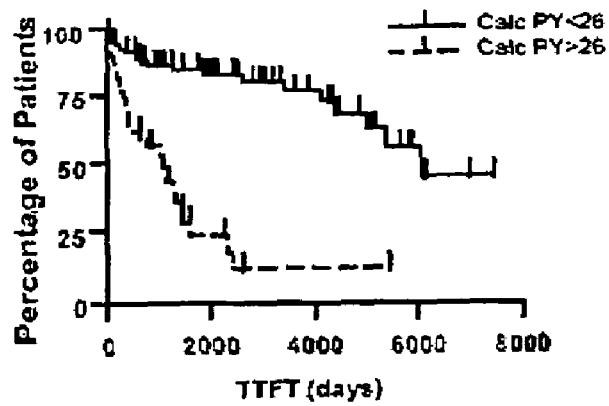
FIG. 3 shows calculated phosphotyrosine identifies more patients with poorer prognosis. Kaplan-Meier analysis of time to first treatment in individuals with chronic lymphocytic leukaemia with high (>26) or low (<26) calculated phosphotyrosine from an unselected dataset of 155 patients, Kaplan-Meier curve showing the association between the capacity of CLL cells to activate NF-κB (as defined by calculated protein tyrosine phosphorylation) and time to first treatment (FIG. 3A), in the subset of Stage A patients only, Kaplan-Meier curve showing the association between the capacity of CLL cells to activate NF-κB (as defined by calculated protein tyrosine phosphorylation) and time to first treatment in Stage A patients only (FIG. 3B), and in patients with mutated $V_H$ genes, Kaplan-Meier curve showing the association between the capacity of CLL cells to activate NF-κB (as defined by calculated protein tyrosine phosphorylation) and time to first treatment in patients with mutated $V_H$ genes only (FIG. 3C)
Figure 3B:
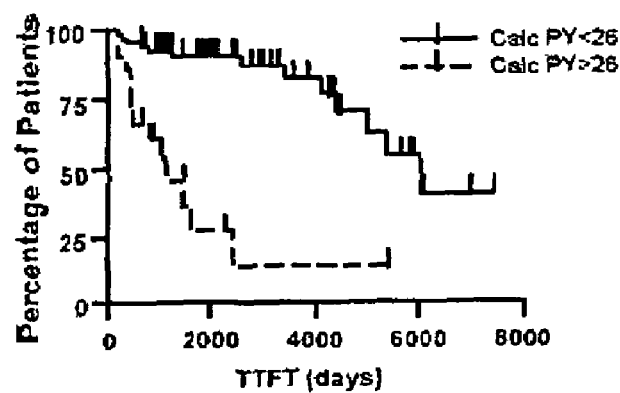
Figure 3C:
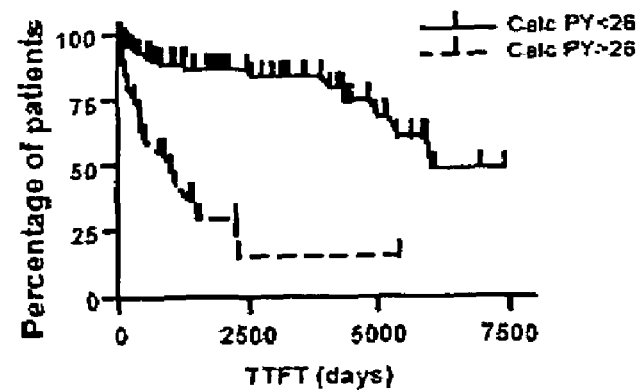
Figure 4A:
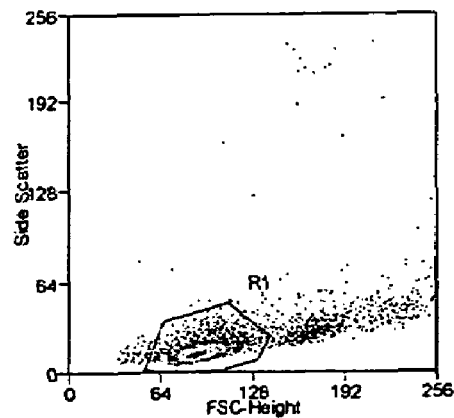
FIG. 4A shows gating using forward scatter and side scatter.
Figure 4B:
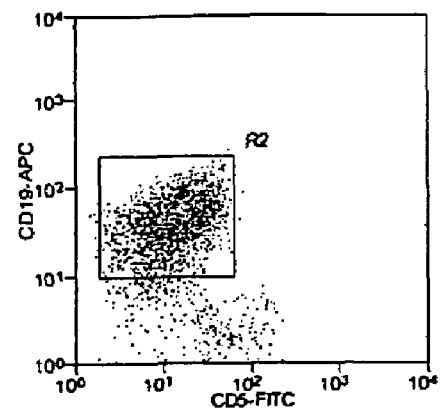
FIG. 4B shows the gating applied to a CD5/CD19 dot plot and the drawing of a second gate around the CD5/CD19 double positive lymphotcytes.
Figure 4C:
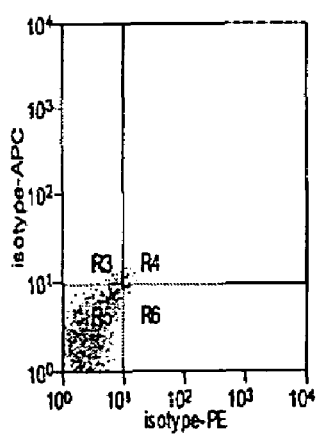
FIG. 4C shows the application of this gate to a CD38/CD19 plot.
Figure 4D:
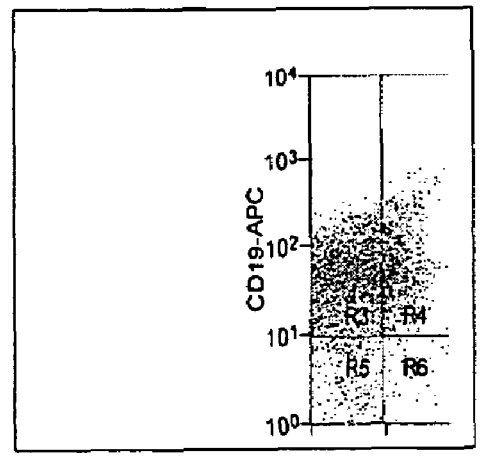
FIG. 4D shows the isotype matched control plot of CD38/CD19 which is used to quantify, with respect to FIG. 4C, the percentage of CD38 positive CLL cells.

Having demonstrated that calculated phosphotyrosine set a threshold for NF-κB, which in turn regulates CLL cell survival, we investigated whether calculated phosphotyrosine could predict patient prognosis. To test this we used a larger database of 155 patients on which we have measured all of the prognostic markers and had information about the patients clinical course. We used the equation, described above to calculate phosphotyrosine as a function of the three prognostic markers, and set a threshold at a calculated phosphotyrosine greater than 26. This is above the threshold that is required to result in activation of NF-κB and thus would increase cell survival. Dividing patients in this way identified patients with a shorter time to first treatment. The Kaplan Meier analysis (FIG. 3a) shows that patients with a calculated phosphotyrosine higher than 26 have a significantly shorter time to first treatment than patients with a calculated phosphotyrosine lower than 26 ($p<0.0001$). The shape of these curves and the median time to first treatment for patients with a high calculated phosphotyrosine (1080 days) is very similar to patients with unmutated $V_H$ genes (1085 days). However, calculated phosphotyrosine greater than 26 identifies more patients (55/155) with adverse prognosis than analysis of unmutated $V_H$ genes alone which only identifies 27 patients from our cohort. We analysed Binet stage A patients in our database (FIG. 3B) and patients with mutated $V_H$ genes (FIG. 3C). In both of these cases, high calculated phosphotyrosine was able to significantly differentiate patients with an early time to first treatment.

This study has identified three important points about the biology of chronic lymphocytic leukaemia cells. Firstly, our data shows that tyrosine phosphorylation integrates two distinct pathways: CD38 expression reflecting the basal tyrosine phosphorylation, while Zap-70 and VH status reflect the ability of the cell to respond to BCR ligation. Secondly, phosphotyrosine sets a threshold above which BCR ligation can activate NF-κB. Interestingly, below this threshold BCR ligation is capable of repressing NF-κB, the first time this has been observed in a human pathology. Thirdly, the strong correlation between IgM regulation of NF-κB and IgM-mediated control of cell survival shows the critical link between these two events. This link and our NF-κB inhibition studies show that NF-κB is likely to be a valuable therapeutic target.

The most important aspect of this study is our integration of the three prognostic markers to improve the identification of patients that will require early intervention. In stage A patients, with mutated VH genes, high CD38 and ZAP-70 expression and adverse cytogenetics, such as 17p and 11q deletions, is uncommon making it currently impossible to identify those patients with unfavourable prognosis. Our equation, integrating the three prognostic markers, makes the identification of patients that have unfavourable prognosis, with stage A disease and mutated $V_H$ genes, possible for the first time.

Figure 5:
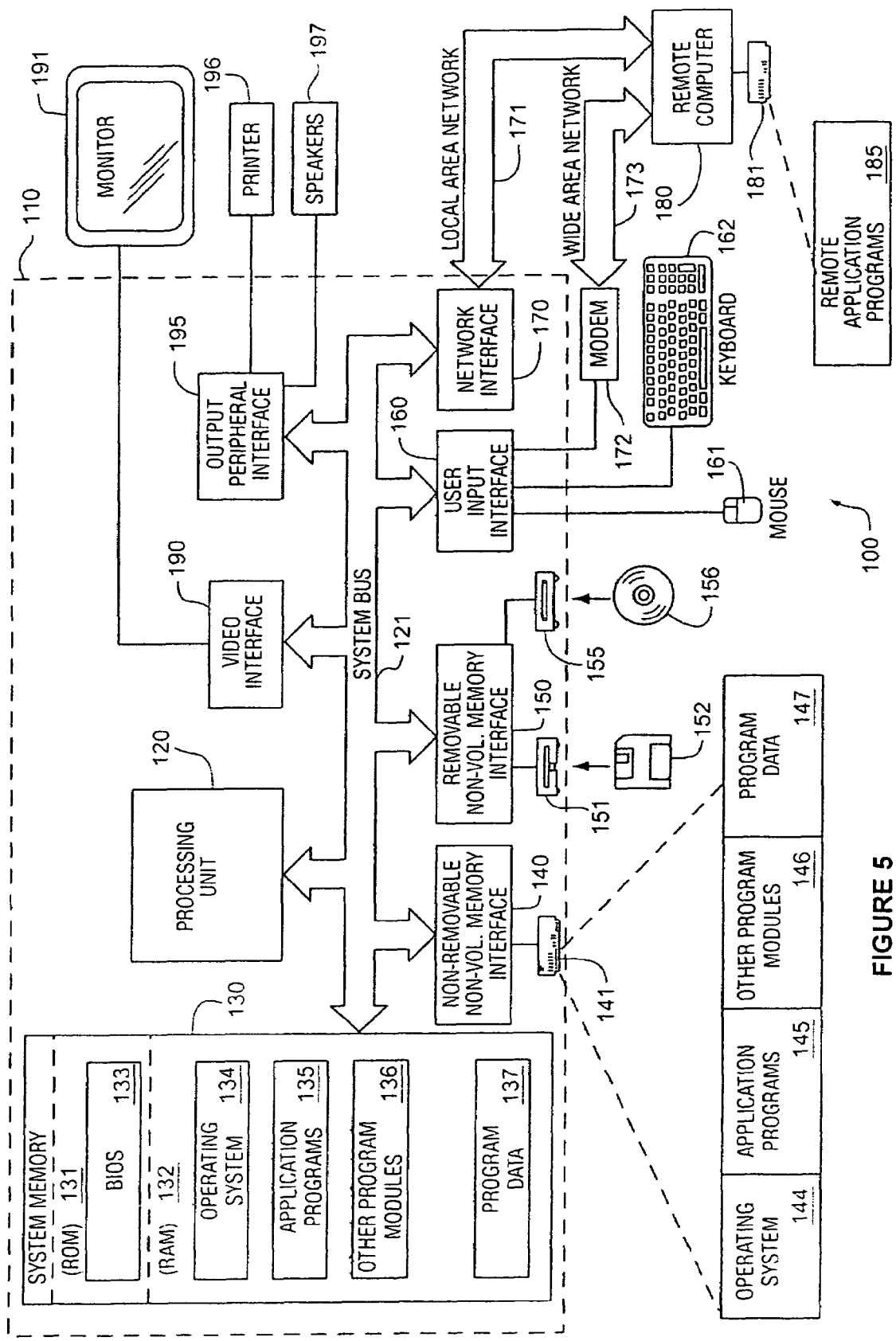
FIG. 5 is a block diagram of a computing system that may operate in accordance with the invention.

FIG. 5 illustrates an example of a suitable computing system environment 100 on which a system for the steps of the claimed method and apparatus may be implemented. The computing system environment 100 is only one example of a suitable computing environment and is not intended to suggest any limitation as to the scope of use or functionality of the method of apparatus of the claims. Neither should the computing environment 100 be interpreted as having any dependency or requirement relating to any one or combination of components illustrated in the exemplary operating environment 100.

The steps of the claimed method and apparatus are operational with numerous other general purpose or special purpose computing system environments or configurations. Examples of well known computing systems, environments, and/or configurations that may be suitable for use with the methods or apparatus of the claims include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The steps of the claimed method and apparatus may be described in the general context of computer-executable instructions, such as program modules, being executed by a computer. Generally, program modules include routines, programs, objects, components, data structures, etc. that perform particular tasks or implement particular abstract data types. The methods and apparatus may also be practiced in distributed computing environments where tasks are performed by remote processing devices that are linked through a communications network. In a distributed computing environment, program modules may be located in both local and remote computer storage media including memory storage devices.

With reference to FIG. 5, an exemplary system for implementing the steps of the claimed method and apparatus includes a general purpose computing device in the form of a computer 110. Components of computer 110 may include, but are not limited to, a processing unit 120, a system memory 130, and a system bus 121 that couples various system components including the system memory to the processing unit 120. The system bus 121 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 110 typically includes a variety of computer readable media. Computer readable media can be any available media that can be accessed by computer 110 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 110. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 130 includes computer storage media in the form of volatile and/or nonvolatile memory such as read only memory (ROM) 131 and random access memory (RAM) 132. A basic input/output system 133 (BIOS), containing the basic routines that help to transfer information between elements within computer 110, such as during start-up, is typically stored in ROM 131. RAM 132 typically contains data and/or program modules that are immediately accessible to and/or presently being operated on by processing unit 120. By way of example, and not limitation, FIG. 5 illustrates operating system 134, application programs 135, other program modules 136, and program data 137.

The computer 110 may also include other removable/non-removable, volatile/nonvolatile computer storage media. By way of example only, FIG. 5 illustrates a hard disk drive 140 that reads from or writes to non-removable, nonvolatile magnetic media, a magnetic disk drive 151 that reads from or writes to a removable, nonvolatile magnetic disk 152, and an optical disk drive 155 that reads from or writes to a removable, nonvolatile optical disk 156 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 141 is typically connected to the system bus 121 through a non-removable memory interface such as interface 140, and magnetic disk drive 151 and optical disk drive 155 are typically connected to the system bus 121 by a removable memory interface, such as interface 150.

The drives and their associated computer storage media discussed above and illustrated in FIG. 5, provide storage of computer readable instructions, data structures, program modules and other data for the computer 110. In FIG. 5, for example, hard disk drive 141 is illustrated as storing operating system 144, application programs 145, other program modules 146, and program data 147. Note that these components can either be the same as or different from operating system 134, application programs 135, other program modules 136, and program data 137. Operating system 144, application programs 145, other program modules 146, and program data 147 are given different numbers here to illustrate that, at a minimum, they are different copies. A user may enter commands and information into the computer 20 through input devices such as a keyboard 162 and pointing device 161, commonly referred to as a mouse, trackball or touch pad. Other input devices (not shown) may include a microphone, joystick, game pad, satellite dish, scanner, or the like. These and other input devices are often connected to the processing unit 120 through a user input interface 160 that is coupled to the system bus, but may be connected by other interface and bus structures, such as a parallel port, game port or a universal serial bus (USB). A monitor 191 or other type of display device is also connected to the system bus 121 via an interface, such as a video interface 190. In addition to the monitor, computers may also include other peripheral output devices such as speakers 197 and printer 196, which may be connected through an output peripheral interface 190.

The computer 110 may operate in a networked environment using logical connections to one or more remote computers, such as a remote computer 180. The remote computer 180 may be a personal computer, a server, a router, a network PC, a peer device or other common network node, and typically includes many or all of the elements described above relative to the computer 110, although only a memory storage device 181 has been illustrated in FIG. 5. The logical connections depicted in FIG. 5 include a local area network (LAN) 171 and a wide area network (WAN) 173, but may also include other networks. Such networking environments are commonplace in offices, enterprise-wide computer networks, intranets and the Internet.

When used in a LAN networking environment, the computer 110 is connected to the LAN 171 through a network interface or adapter 170. When used in a WAN networking environment, the computer 110 typically includes a modem 172 or other means for establishing communications over the WAN 173, such as the Internet. The modem 172, which may be internal or external, may be connected to the system bus 121 via the user input interface 160, or other appropriate mechanism. In a networked environment, program modules depicted relative to the computer 110, or portions thereof, may be stored in the remote memory storage device. By way of example, and not limitation, FIG. 5 illustrates remote application programs 185 as residing on memory device 181. It will be appreciated that the network connections shown are exemplary and other means of establishing a communications link between the computers may be used.

Figure 6:
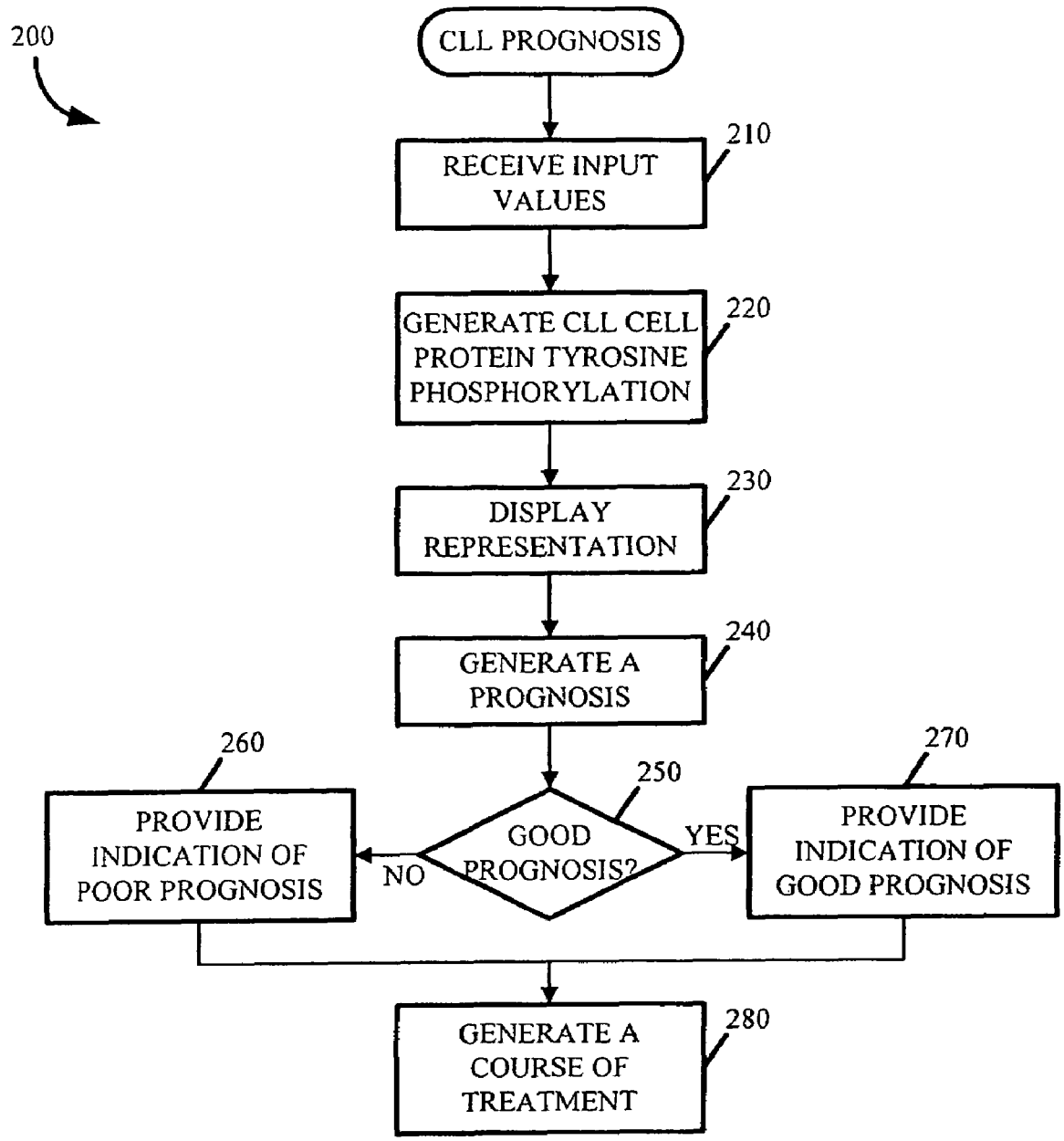
FIG. 6 is an example of a CLL prognosis routine for determining a prognosis of a patient presenting with chronic lymphocytic leukaemia (CLL).

FIG. 6 is an illustration of a CLL prognosis routine 200 for determining a prognosis of a patient presenting with chronic lymphocytic leukaemia (CLL), as provided in greater detail above. All or part of the method 200 may be implemented as one or more routines, which may be provided on a computer readable medium and/or operational with a computing system where the routine is adapted to be executed by a processor. The routine 200 may be implemented using any suitable programming languages and techniques.

Referring to FIG. 6, the routine 200 begins at block 210 where input values are received for measurements of a $V_H$ gene mutation status ($V_H$), CD38 expression (CD38), and ZAP-70 expression (ZAP70) obtained from lymphocytes of a human with chronic lymphcytic leukaemia (CLL). For example, information concerning the $V_H$ gene status of an individual, information concerning the expression of CD38 in CLL cells taken from the patient, and information concerning the expression of the ZAP-70 in CLL cells taken from the patient may be inserted into a computer, such as the computer 110 of FIG. 5, using a variety of means, including, but not limited to, a removable memory interface 150, a user input interface 160, a network interface 170 or other devices for receiving information at the computer 110.

At block 220, a CLL cell protein tyrosine phosphorylation ($PY_{PostIgM}$) is generated from the measurements received at block 210. The $PY_{PostIgM}$ generated at block 220 may be calculated as a sum based upon the measurements according to the weighted relationship:

$$(1.96 \pm 0.19)\sqrt{CD38} : (0.39 \pm 0.03)V_H : (0.13 \pm 0.01)ZAP70$$

where:

CD38=the CLL cell surface presence of CD38, expressed as % of CLL cells with greater fluorescence than an isotype-matched control, VH status=VH gene mutation status, expressed as % homology to the closest germline sequence, and ZAP70=CLL cell ZAP-70 expression, expressed as % of CLL cells with equal or greater fluorescence than the T-cell population in the same sample.

The $PY_{PostIgM}$ may be calculated according to the following formula:

$$PY_{PostIgM} = (-26.95 \pm 2.69) + ((1.96 \pm 0.19)\sqrt{CD38}) + ((0.39 \pm 0.03)V_H \text{status}) + ((0.13 \pm 0.01)ZAP70)$$

At block 230, a representation of the $PY_{PostIgM}$ generated at block 220 may be displayed on a display unit, such as the monitor 191 of FIG. 5. The representation may be provided as an alphanumeric display and/or as a graphical display. In particular, the representation may be provided by a user interface routine which provides a graphical user interface (GUI) and which may be implemented via a computing system, such as the computer 110. It should be recognized that the GUI may include one or more software routines that are implemented using any suitable programming languages and techniques.

At block 240, a prognosis for the patient with CLL may be generated based upon the $PY_{PostIgM}$ generated at block 220. The routine 200 may determine whether the prognosis generated at block 240 is a good prognosis or a poor prognosis at block 250. For example, the determination at block 250 may include determining whether the phosphorylation status is above or below a certain threshold. In the formula indicated above, the threshold may be 26±2.6. Alternatively, the threshold is where the expression:

$$((1.96 \pm 0.19)\sqrt{CD38}) + ((0.39 \pm 0.03)V_H \text{status}) + ((0.13 \pm 0.01)ZAP70)$$

is greater than 50, and, more particularly, where the above expression is greater than 52.95.

If the phosphorylation status is above the threshold, as determined at block 250, the routine 200 may determine that the prognosis of the patient is poor, and provide an indication that the prognosis is poor at block 260. As explained in further detail above, an elevated $PY_{PostIgM}$ correlates with a poor prognosis. If the phosphorylation status is below the threshold, as determined at block 250, the routine 200 may determine that the prognosis of the patient is good, and provide an indication that the prognosis is good at block 270. At block 280, a course of treatment for the patient may be generated based upon the $PY_{PostIgM}$ generated at block 220 or based upon the prognosis generated at block 240.

1. Shanafelt, T. D., Geyer, S. M. & Kay, N. E. Prognosis at diagnosis: integrating molecular biologic insights into clinical practice for patients with CLL. *Blood* 103, 1202-10 (2004).
2. Damle, R. N. et al. B-cell chronic lymphocytic leukemia cells express a surface membrane phenotype of activated, antigen-experienced B lymphocytes. *Blood* 99, 4087-93 (2002).
3. Durig, J. et al. ZAP-70 expression is a prognostic factor in chronic lymphocytic leukemia. *Leukemia* 17, 2426-34 (2003).
4. Faderl, S. et al. Expression profile of 11 proteins and their prognostic significance in patients with chronic lymphocytic leukemia (CLL). *Leukemia* 16, 1045-52 (2002).
5. Hamblin, T. J. et al. CD38 expression and immunoglobulin variable region mutations are independent prognostic variables in chronic lymphocytic leukemia, but CD38 expression may vary during the course of the disease. *Blood* 99, 1023-9 (2002). 11
6. Montserrat, E. & Rozman, C. Chronic lymphocytic leukaemia: prognostic factors and natural history. *Baillieres Clin Haematol* 6, 849-66 (1993).
7. Damle, R. N. et al. Ig V gene mutation status and CD38 expression as novel prognostic indicators in chronic lymphocytic leukemia. *Blood* 94, 1840-7 (1999).
8. Hamblin, T. J., Davis, Z., Gardiner, A., Oscier, D. G. & Stevenson, F. K. Unmutated Ig V(H) genes are associated with a more aggressive form of chronic lymphocytic leukemia. *Blood* 94, 1848-54 (1999).
9. Rassenti, L. Z. et al. ZAP-70 compared with immunoglobulin heavy-chain gene mutation status as a predictor of disease progression in chronic lymphocytic leukemia. *N Engl J Med* 351, 893-901 (2004).
10. Ghia, P. et al. The pattern of CD38 expression defines a distinct subset of chronic lymphocytic leukemia (CLL) patients at risk of disease progression. *Blood* 101, 1262-9 (2003).
11. Hivroz, C., Grillot-Courvalin, C., Labaume, S., Miglierina, R. & Brouet, J. C. Cross-linking of membrane IgM on B CLL cells: dissociation between intracellular free Ca2+ mobilization and cell proliferation. *Eur J Immunol* 18, 1811-7 (1988).
12. Lanham, S. et al. Differential signaling via surface IgM is associated with VH gene mutational status and CD38 expression in chronic lymphocytic leukemia. *Blood* 101, 1087-93 (2003).
13. Zupo, S. et al. CD38 expression distinguishes two groups of B-cell chronic lymphocytic leukemias with different responses to anti-IgM antibodies and propensity to apoptosis. *Blood* 88, 1365-74 (1996).
14. Chen, L. et al. ZAP-70 directly enhances IgM signaling in chronic lymphocytic leukemia. *Blood* 105, 2036-41 (2005).
15. Petlickovski, A. et al. Sustained signaling through the B-cell receptor induces Mcl-1 and promotes survival of chronic lymphocytic leukemia B cells. *Blood* 105, 4820-7 (2005). 12
16. Furman, R. R., Asgary, Z., Mascarenhas, J. O., Liou, H. C. & Schattner, E. J. Modulation of NF-kappa B activity and apoptosis in chronic lymphocytic leukemia B cells. *J Immunol* 164, 2200-6 (2000).

17. Palke, A., Mecklenbrauker, I. & Tarakhovsky, A. Survival signaling in resting B cells. *Curr Opin Immunol* 16, 251-5 (2004).
18. Cuni, S. et al. A sustained activation of PI3K/NF-kappaB pathway is critical for the survival of chronic lymphocytic leukemia B cells. *Leukemia* 18, 1391-400 (2004).
19. Romano, M. F., Lamberti, A., Turco, M. C. & Venuta, S. CD40 and B chronic lymphocytic leukemia cell response to fludarabine: the influence of NF-kappaB/Rel transcription factors on chemotherapyinduced apoptosis. *Leuk Lymphoma* 36, 255-62 (2000).
20. Ku, P. T., You, M. & Bose, H. R., Jr. Role and regulation of Rel/NF-kappaB activity in antiimmunoglobulin-induced apoptosis in WEHI-231 B lymphoma cells. *Cell Signal* 12, 245-53 (2000).
21. Tian, M. T., Gonzalez, G., Scheer, B. & DeFranco, A. L. Bcl10 can promote survival of antigenstimulated B lymphocytes. *Blood* 106, 2105-12 (2005).
22. Nedellec, S. et al. B cell response to surface IgM cross-linking identifies different prognostic groups of B-chronic lymphocytic leukemia patients. *J Immunol* 174, 3749-56 (2005).
23. Mori, N. et al. Bay 11-7082 inhibits transcription factor NF-kappaB and induces apoptosis of HTLVI-infected T-cell lines and primary adult T-cell leukemia cells. *Blood* 100, 1828-34 (2002).
24. Brennan, P. & O'Neill, L. A. Inhibition of nuclear factor kappaB by direct modification in whole cells—mechanism of action of nordihydroguaiaritic acid, curcumin and thiol modifiers. *Biochem Pharmacol* 55, 965-73 (1998).

What is claimed is:

1. A method for determining the prognosis of a patient presenting with chronic lymphocytic leukaemia comprising:
  a) isolating a population of lymphocytes from a blood sample taken from said patient;
  b) examining the DNA of said lymphocytes in order to determine the $V_H$ gene mutation status, wherein the $V_H$ gene mutation status is expressed as a percentage homology to the closest germline sequence;
  c) detecting the expression of CD38 on said lymphocytes, wherein the expression is expressed as a percentage of CLL cells with greater fluorescence than the isotype-matched control;
  d) detecting the expression of ZAP-70 by said lymphocytes, wherein the expression is expressed as a percentage of CLL cells with equal or greater fluorescence than the T-cell population in the blood sample; and
  e) feeding the percentages from steps b), c) and d) into the following equation in order to determine the protein tyrosine phosphorylation of said lymphocytes:

$$PY_{PostIgM} = (-26.95 \pm 2.69) + ((1.96 \pm 0.19)\sqrt{CD38}) + ((0.39 \pm 0.03)V_H \text{status}) + ((0.13 \pm 0.01)\text{ZAP70}),$$

where $PY_{PostIgM}$ is CLL cell protein tyrosine phosphorylation (following IgM stimulation), CD38 is CLL cell surface presence of CD38, $V_H$ status is $V_H$ gene mutation status, and ZAP-70 is CLL cell ZAP-70 expression;
  f) indicating the prognosis for said patient is poor when said protein tyrosine phosphorylation is above the threshold 26±2.6.

2. A method according to claim 1 wherein $((1.96\pm0.19)\sqrt{CD38}) + ((0.39\pm0.03)V_H\text{status}) + ((0.13\pm0.01)\text{ZAP70})$ is greater than 52.95.

3. A method according to claim 1 wherein part c) above involves quantifying the amount of CD38 on the surface of said lymphocytes.

4. A method for treating an individual presenting with chronic lymphocytic leukaemia comprising:
  a) isolating a population of lymphocytes from a blood sample taken from said patient;
  b) examining the DNA of said lymphocytes in order to determine the $V_H$ gene mutation status, wherein the $V_H$ gene mutation status is expressed as a percentage homology to the closest germline sequence;
  c) detecting the expression of CD38 on said lymphocytes, wherein the expression is expressed as a percentage of CLL cells with greater fluorescence than the isotype-matched control;
  d) detecting the expression of ZAP-70 by said lymphocytes, wherein the expression is expressed as a percentage of CLL cells with equal or greater fluorescence than the T-cell population in the blood sample; and
  e) feeding the percentages from steps b), c) and d) into the following equation in order to determine the protein tyrosine phosphorylation of said lymphocytes:

$$PY_{PostIgM} = (-26.95 \pm 2.69) + ((1.96 \pm 0.19)\sqrt{CD38}) + ((0.39 \pm 0.03)V_H \text{status}) + ((0.13 \pm 0.01)\text{ZAP70}),$$

where $PY_{PostIgM}$ is CLL cell protein tyrosine phosphorylation (following IgM stimulation), CD38 is CLL cell surface presence of CD38, $V_H$ status is $V_H$ gene mutation status, and ZAP-70 is CLL cell ZAP-70 expression;
  f) indicating the prognosis for said patient is poor when said protein tyrosine phosphorylation is above the threshold 26±2.6 and so prescribing immediate treatment to combat the disease.

5. A method for determining the prognosis of a patient presenting with chronic lymphocytic leukaemia comprising:
  a) examining the DNA of lymphocytes isolated from said patient in order to determine the $V_H$ gene mutation status, wherein the $V_H$ gene mutation status is expressed as a percentage homology to the closest germline sequence;
  b) detecting the expression of CD38 on said lymphocytes, wherein the expression is expressed as a percentage of CLL cells with greater fluorescence than the isotype-matched control;
  c) detecting the expression of ZAP-70 by said lymphocytes, wherein the expression is expressed as a percentage of CLL cells with equal or greater fluorescence than the T-cell population in the blood sample; and
  d) feeding the percentages from steps a), b) and c) into the following equation in order to determine the protein tyrosine phosphorylation of said lymphocytes:

$$PY_{PostIgM} = (-26.95 \pm 2.69) + ((1.96 \pm 0.19)\sqrt{CD38}) + ((0.39 \pm 0.03)V_H \text{status}) + ((0.13 \pm 0.01)\text{ZAP70}),$$

where $PY_{PostIgM}$ is CLL cell protein tyrosine phosphorylation (following IgM stimulation), CD38 is CLL cell surface presence of CD38, $V_H$ status is $V_H$ gene mutation status, and ZAP-70 is CLL cell ZAP-70 expression;
  d) indicating the prognosis for said patient is poor or good, wherein said prognosis is poor when said protein tyrosine phosphorylation is above the threshold 26±2.6.

* * * * *